US006485933B1

(12) United States Patent
Bandman et al.

(10) Patent No.: US 6,485,933 B1
(45) Date of Patent: Nov. 26, 2002

(54) B CELL RECEPTOR ASSOCIATED PROTEINS

(75) Inventors: Olga Bandman, Mountain View; Jennifer L. Hillman, San Jose; Surya K. Goli, Sunnyvale; Sherry A. Capitant, Los Altos, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 08/851,971

(22) Filed: May 7, 1997

(51) Int. Cl.$^7$ ............... C07H 21/02; C07H 21/04; C12N 15/12; C12N 15/79
(52) U.S. Cl. ............ 435/69.1; 435/6; 435/325; 435/320.1; 435/91.5; 435/91.1; 435/91.2; 536/23.1; 536/23.5; 536/23.2; 536/24.3; 536/24.31; 530/395
(58) Field of Search ............... 536/23.1, 23.5, 536/23.2, 24.3, 24.31; 435/320.1, 69.1, 325, 6, 91.1, 91.2, 91.5; 530/395

(56) References Cited

FOREIGN PATENT DOCUMENTS

WO          98/31799          7/1998

OTHER PUBLICATIONS

Wells et al., J. Leuko. Biol., 61: 545–550, 1997.*
Gerhold et al., Bio Essays, 18: 973–981, 1996.*
Ansari–Lari, M.A., et al., (GI 1922935), GenBank Sequence Database (Accession AAB51324), National Center for Biotechnology Information, National Library of Medicine, Bethesda, Maryland 20894 (Jan. 5, 2001) end).
Adachi, T. et al., "The specificity of association of the IgD molecule with the accessory proteins BAP31/BAP29 lies in the IgD transmembrane sequence". The EMBO Journal, vol. 15, No. 7, 1996, pp. 1534–1541, XP002073021.
Li, E. et al, "Molecular Cloning and Characterization of a transmembrane surface antigen in human cells". Euorpean Journal of Biochemistry, vol. 238, No. 3, Jun. 1996.
Database EMBL Emest2, Entry AA701660, Accession No. AA701660, Dec. 22, 1997, XP002073030.
Database EMBL, Emest4, Entry AA936326, Accession No. AA936326, Apr. 30, 1998, XP002073031.
Database EMBL Emest8, Entry HS1316344, Accession No. AA524665, Jul. 19, 1997, XP002073032.
Carsetti, R. et al., "A role for immunoglobulin D: interference with tolerance induction." *Eur.J.Immunol.* (1993) 23:168–178.
Roes, J. et al., "Immunoglobulin D (IgD)–deficient Mice Reveal an Auxiliary Receptor Function for IgD in Antigen–mediated Recruitment of B Cells." *J.Exp.Med.* (1993) 177:45–55.
Kim, K. et al., "Regulation of Cell Division of Mature B Cells by Ionomycin and Phorbol Ester" *J.Immuno.* (1992) 148:1797–1803.
Kim, K. et al., "Two new proteins preferentially associated with membrane immunoglobulin D." *EMBO J.* (1994) 13(16):3793–3800.
Terashima, M. et al., "The IgM antigen receptor of B lymphocytes is associated with prohibitin and a prohibitin–related protein." *Embo J.* (1994) 13(16):3782–3792. (GI 541734).
Ansari–Lari, M. et al., "A Gene–rich Cluster between the CD4 and Triosephosphate Isomerase Genes at Human Chromosome 12p13." *Genome Research* (1996) 6:314–326. (GI 1732420).

* cited by examiner

Primary Examiner—Ronald B. Schwadron
(74) Attorney, Agent, or Firm—Incyte Genomics, Inc.

(57) ABSTRACT

The present invention provides B cell receptor associated proteins (BCRP) and polynucleotides which identify and encode BCRP. The invention also provides expression vectors, host cells, agonists, antibodies, and antagonists. The invention also provides methods for treating disorders associated with expression of BCRP.

11 Claims, 10 Drawing Sheets

```
     9         18        27        36        45        54
5' TGC TGT GGG AGA GTT CGG TTG CTG CGG GGC CTG CAC GTT GAC TGT GGG AAA 63        72        81        90        99        108
CTC GGA AAC AAG CTC ACA TCT TCC TGT GGG AAA CCT TCT AGC AAC AGG ATG AGT
                                                                  M   S 117       126       135       144       153       162
CTG CAG TGG ACT GCA GTT GCC ACC TTC CTC TAT GCG GAG GTC TTT GTT GTG TTG
 L   Q   W   T   A   V   A   T   F   L   Y   A   E   V   F   V   V   L 171       180       189       198       207       216
CTT CTC TGC ATT CCC TTC ATT TCT CCT AAA AGA TGG AAC CAG AAG ATT TTT TCA TTT
 L   L   C   I   P   F   I   S   P   K   R   W   N   Q   K   I   F   S   F 225       234       243       252       261       270
AAT GTC TGG GGT AAA ATT GCA ACT TTT TGG AAC AAG GCT TTC CTT ACC ATT ATC
 N   V   W   G   K   I   A   T   F   W   N   K   A   F   L   T   I   I 279       288       297       306       315       324
ATC CTA TTG ATT GTT CTA TTT CTA GAT GCT GTG AGA GAA GTA AGG AAA TAT TCC
 I   L   L   I   V   L   F   L   D   A   V   R   E   V   R   K   Y   S 333       342       351       360       369       378
TCA GTT CAT ACC ATT GAG AAG AGC ACC AGC AGA GAA CCT GAT GCC TAT GAA CAC
 S   V   H   T   I   E   K   S   T   S   R   E   P   D   A   Y   E   H
```

FIGURE 1A

```
 387       396       405       414       423       432
ACA CAG ATG AAA CTT TTT AGG TCT CAA AGA AAT CTT TAC ATT TCT GGA TTT TCC
 T   Q   M   K   L   F   R   S   Q   R   N   L   Y   I   S   G   F   S 441       450       459       468       477       486
CTA TTT TTT TGG CTA GTT TTG AGA CGT CTG GTT ACG CTT ATT ACT CAA CTG GCA
 L   F   F   W   L   V   L   R   R   L   V   T   L   I   T   Q   L   A 495       504       513       522       531       540
AAA GAA CTG TCA AAC AAA GGT GTA CTT AAA ACT CAA GCA GAA AAT ACT AAC AAG
 K   E   L   S   N   K   G   V   L   K   T   Q   A   E   N   T   N   K 549       558       567       576       585       594
GCT GCC AAA AAA TTT ATG GAA GAA AAC CTA AAA ACT GAA AAA AGG ATT TTG AAA AGC
 A   A   K   K   F   M   E   E   N   L   K   T   E   K   R   I   L   K   S 603       612       621       630       639       648
CAT GGT AAA GAT GAA GAA TGT GTT TTG GAA GCA AAT AAA CTA AAA CTA GTA GAA
 H   G   K   D   E   E   C   V   L   E   A   N   K   L   K   L   V   E 657       666       675       684       693       702
GAC GAG AAA CTG AAA ACT GAA TTA AGG AAG ACT TCA GAT GCC CTT TCT AAG
 D   E   K   L   K   T   E   L   R   K   T   S   D   A   L   S   K 711       720       729       738       747       756
CAT AAT GAT GTG ATG AAG ATG GAA ATG CAG TCA GAG AGA CTT TCG AAA GAA
 N   N   D   V   M   K   M   E   M   Q   S   E   R   L   S   K   E
```

FIGURE 1B

```
       765             774             783             792             801             810
TAT GAT CAA CTC CTG AAA GAA CAC TCT GAA CTT CAG GAT CGT TTA GAA AGA GGC
 Y   D   Q   L   L   K   E   H   S   E   L   Q   D   R   L   E   R   G 819             828             837             846             855             864
AAC AAG AAA AGA CTG TGA ACT TTA TAA AAG ACA CTT GCA ATA TAC TGT GTC AAA
 N   K   K   R   L 873             882             891             900             909             918
ATG ATA ATT TTG TTA TGT TAG CCT CTA GAA AAT TTA AGT TCA GAA AAA TGC ACT 927             936             945
ATG ACC GGT TCG TAA TTT TTT TAA TGC C 3'
```

FIGURE 1C

```
                                                                                     54
5' GGG AGG GTT TCA AAG GGA GCG CAC TTC CGC TGC CCT TTC TTT CGC CAG CCT TAC
                 9       18              27              36              45

108
   GGG CCC GAA CCC TCG TGT GAA GGG TGC AGT ACC TAA GCC GGA GCG GGG TAG AGG
        63              72              81              90              99

162
   CGG GCC GGC ACC CCC TTC TGA CCT CCA GTG CCG GCC TCA AGA TCA GAC ATG
                117             126             135             144     153      M

216
   GCC CAG AAC TTG AAG GAC TTG GCG GGA CGG CTG CCC GCC GGG CCC CGG GGC ATG
    A   Q   N   L   K   D   L   A   G   R   L   P   A   G   P   R   G   M
                171             180             189             198     207

270
   GGC ACG GCC CTG AAG CTG TTG CTG GGG GCC GGC GTG GCC GTG TAC GGT GTG CGC
    G   T   A   L   K   L   L   L   G   A   G   V   A   V   Y   G   V   R
                225             234             243             252     261

324
   GAA TCT GTG TTC ACC GTG GAA GGC CAC AGA GCC ATC TTC TTC AAT CGG ATC
    E   S   V   F   T   V   E   G   H   R   A   I   F   F   N   R   I
                279             288             297             306     315

378
   GGT GGA CAG CAG GAC ACT ATC CTG GCC GAG GGC CTT CAC TTC AGG ATC CCT
    G   G   Q   Q   D   T   I   L   A   E   G   L   H   F   R   I   P
                333             342             351             360     369

FIGURE 2A
```

| 387 | | 396 | | 405 | | 414 | | 423 | | 432 | |
|---|---|---|---|---|---|---|---|---|---|---|---|
| TGG | TTC | CAG | TAC | CCC | ATT | ATC | TAT | GAC | ATT | CGG | GCC | AGA | CCT | CGA | AAA | ATC | TTC |
| W | F | Q | Y | P | I | I | Y | D | I | R | A | R | P | R | K | I | F |

| 441 | | 450 | | 459 | | 468 | | 477 | | 486 | |
|---|---|---|---|---|---|---|---|---|---|---|---|
| TCC | CCT | ACA | GGG | TTC | AAA | GAC | CTA | CAG | ATG | GTG | AAT | ATC | TNC | CTG | CGA | GTG | TTG |
| S | P | T | G | F | K | D | L | Q | M | V | N | I | X | L | R | V | L |

| 495 | | 504 | | 513 | | 522 | | 531 | | 540 | |
|---|---|---|---|---|---|---|---|---|---|---|---|
| TCT | NGA | AAT | GNT | CAG | GAG | CTT | NCT | AGC | ATG | TAC | CAG | CGG | CTA | GGG | GTG | GTG | GAC |
| S | X | N | X | Q | E | L | X | S | M | Y | Q | R | L | G | V | V | D |

| 549 | | 558 | | 567 | | 576 | | 585 | | 594 | |
|---|---|---|---|---|---|---|---|---|---|---|---|
| TAC | GAG | CGA | GTG | TTG | CCG | TCC | ATT | KTY | AAM | GRG | GTG | CTC | CAG | CGG | AAG | AGT | GTG |
| Y | E | R | V | L | P | S | I | X | X | X | V | L | Q | R | K | S | V |

| 603 | | 612 | | 621 | | 630 | | 639 | | 648 | |
|---|---|---|---|---|---|---|---|---|---|---|---|
| GCC | TTC | AAT | GCC | TCA | CAG | CTG | ATC | ACC | CAG | CGG | GCC | CAG | GTA | TCC | CTG | TTG |
| A | F | N | A | S | Q | L | I | T | Q | R | A | Q | V | S | L | L |

| 657 | | 666 | | 675 | | 684 | | 693 | | 702 | |
|---|---|---|---|---|---|---|---|---|---|---|---|
| ATC | CGC | CGG | GAG | CTG | ACA | GAG | AGG | GCC | AAG | GAC | TTC | AGC | CTC | ATC | CTG | GAT |
| I | R | R | E | L | T | E | R | A | K | D | F | S | L | I | L | D |

| 711 | | 720 | | 729 | | 738 | | 747 | | 756 | |
|---|---|---|---|---|---|---|---|---|---|---|---|
| GTG | GCC | ATC | ACA | GAG | CTG | AGC | TTT | AGC | CGA | GAG | TAC | ACA | GCT | GCT | GTA | GAA | GCC |
| V | A | I | T | E | L | S | F | S | R | E | Y | T | A | A | V | E | A |

FIGURE 2B

```
                            765          774          783          792      801          810
AAA CAA GTG GCC CAG CAG GAG GCC CAG CGG GCC CAA TTC TTG GTA GAA AAA GCA
 K   Q   V   A   Q   Q   E   A   Q   R   A   Q   F   L   V   E   K   A 819          828          837      846          855          864
AAG CAG GAA CAG CGG CAG AAA ATT GTG CAG GCC GAG GGT GAG GCC GAG GCT GCC
 K   Q   E   Q   R   Q   K   I   V   Q   A   E   G   E   A   E   A   A 873          882          891      900          909          918
AAG ATG CTT GGA GAA GCA CTG AGC AAG AAC CCT GGC TAC ATC AAA CTT CGC AAG
 K   M   L   G   E   A   L   S   K   N   P   G   Y   I   K   L   R   K 927          936          945      954          963          972
ATT CGA GCA GCC AAT ATC TYC AAG ACG ATC GCC ACA TCA CAG AAT CGT ATC
 I   R   A   A   N   I   X   K   T   I   A   T   S   Q   N   R   I 981          990          999      1008         1017         1026
TAT CTC ACA GCT GAC AAC CTT GTG CTG AAC CTA CAG GAT GAA AGT TTC ACC AGG
 Y   L   T   A   D   N   L   V   L   N   L   Q   D   E   S   F   T   R 1035         1044         1053     1062         1071         1080
GGA AGT GAC AGC CTC ATC AAG GGT AAG AAA TGA GCC TAG TCA CCA AGA ACT CCA
 G   S   D   S   L   I   K   G   K   K 1089         1098         1107     1116         1125         1134
CCC CCA GAG GAA GTG GAT CTR CTT CTY CAG TTT TTG AGG AGC CAG CCA GGG GTN
```

FIGURE 2C

```
      1143      1152      1161      1170      1179      1188
CAG CAC AGM CCT ACC CCG GCC YAG TAT CAT GCG ATG GTC CCC CAC AAC GGT TTC
      1197      1206      1215
CTG AAC CCT TTT GGA TTA AGG AAG ACT NAA GAT AG 3'
```

B CELL RECEPTOR ASSOCIATED PROTEINS

FIELD OF THE INVENTION

This invention relates to nucleic acid and amino acid sequences of B cell receptor associated proteins and to the use of these sequences in the diagnosis, prevention, and treatment of immunological disorders and cancer.

BACKGROUND OF THE INVENTION

The B-cell response to antigens, which is modulated through receptors, is an essential component of the normal immune system. Immature B cells undergo a selection process based on antigen binding prior to leaving the bone marrow. Mature B cells recognize foreign antigens through B cell receptors (BCR) and produce specific antibodies which bind the foreign antigens. To generate an efficient response to complex antigens, the BCR, BCR associated proteins, and T cell assistance are required. The antigen/receptor complex is internalized, and the antigen is proteolytically processed. A small part of the antigen remains complexed with major histocompatability complex-II (MHCII) molecules on the surface of the B cells where the complex can be recognized by T cells. T cells activated by antigen presentation secrete a variety of lymphokines that induce B cell maturation.

Signaling through the BCR plays an important role in both the generation of antibody and in the establishment of immunological tolerance. Immature B cells that bind self-antigens while still in the bone marrow are eliminated by apoptosis. In contrast, antigen binding on mature B cells results in activation, proliferation, anergy, or apoptosis. The particular functional response depends on whether the B cell receives co-stimulatory signals through other surface receptors and which signal transduction pathways are activated. A mature B cell co-expresses two classes of membrane-bound immunoglobin, IgM and IgD, which have identical cytoplasmic domains and identical antigen binding specificity. In order to be expressed on the B cell surface, the BCR, whether it is of the IgM or IgD class, must be associated with two other polypeptides, Ig-α and Ig-β. The cytoplasmic portions of the IgM/Ig-Ig-α/Ig-β and the IgD/Ig-Ig-α/Ig-β complex should therefore be identical to each other.

Both Ig-α and Ig-β contain a sequence, ITAM (SEQ ID NO:9), that can cause activation of protein tyrosine kinases. In addition, the cytoplasmic tails of Ig-α and Ig-β are sufficient for the internalization of the surface proteins and their targeting to endosomal compartments for processing. Early biochemical events in signal transduction, such as protein kinase activation and release of calcium ions, are similar for the two receptors (IgM and IgD); however their subsequent biological effects, however, are different. Antigen binding or cross-linking of the IgM receptor leads to apoptosis, while binding of IgM and IgD, or IgD alone, does not. Binding to IgD alone induces cell proliferation. Analysis of IgD-deficient mice shows that the absence of IgD reduces the efficacy of B cell participation in immune responses. Further in vitro differences in antibody responses, immunological memory, and tolerance have also been described (Carsetti, R. et al. (1993) Eur. J. Immunol. 23: 168–178; Roes, J. et al. (1 993) J. Expt. Med. 177: 45–55; and Kim, K. M. et al. (1992) J. Immunol. 148: 29–34).

Additional analysis of the receptor complex shows that at least five more proteins are associated with the mouse BCR. B cell associated proteins (BAPs) with a mass of 31, 37, and 41 kDa are specifically associated with IgM, while 29 and 31 kDa BAPs are preferentially associated with IgD. BAP 41 has not been characterized, but BAP 32 and BAP 37 are related to prohibitin, a protein which has been implicated in the control of cell proliferation and may have tumor suppressor activity. Both BAP 32 and 37 interact with IgM via its transmembrane domain and contain a C-terminal NPXY (SEQ ID NO:10) motif associated with internalization of proteins. The IgD-associated BAP 29 and BAP 31 show structural features suggesting that they co-localize with the membrane IgM BCR in the plasma membrane. Northern analysis shows that BAP 29, BAP 31, BAP 32, and BAP 37 are expressed in all tissue types examined, and that BAP 32 and BAP 37 are expressed more strongly in transformed cell lines than in normal tissues (Kim, K.-M., et al. (1994) EMBO J.13: 3793–3800; and Terashima, M., et al. (1994) EMBO J.13: 3782–3792).

The discovery of new B-cell receptor associated proteins and the polynucleotides encoding them satisfies a need in the art by providing new compositions which are useful in the diagnosis, prevention and treatment of cancer and immunological disorders.

SUMMARY OF THE INVENTION

The present invention features a B-cell receptor-associated protein hereinafter designated BCRP1 and characterized as having similarity to mouse BAP 29.

Accordingly, the invention features a substantially purified BCRP1 having the amino acid sequence shown in SEQ ID NO:1.

One aspect of the invention features isolated and substantially purified polynucleotides that encode BCRP1. In a particular aspect, the polynucleotide is the nucleotide sequence of SEQ ID NO:2.

The invention also relates to a polynucleotide sequence comprising the complement of SEQ ID NO:2 or variants thereof. In addition, the invention features polynucleotide sequences which hybridize under stringent conditions to SEQ ID NO:2.

The present invention additionally features a B-cell receptor-associated protein hereinafter designated BCRP2 and characterized as having similarity to mouse BAP 37.

Accordingly, the invention features a substantially purified BCRP2 having the amino acid sequence shown in SEQ ID NO:3. The invention also features a polypeptide variant of BCRP2, SEQ ID NO:5, where $F_{91}$ and $F_{96}$ are replaced by S, and $V_{126}$ is replaced by L.

One aspect of the invention features isolated and substantially purified polynucleotides that encode BCRP2 and the BCRP2 variant (SEQ ID NO:4 and SEQ ID NO:6).

The invention also features polynucleotide sequences comprising the complement of SEQ ID NO:4, SEQ ID NO:6, or variants thereof. In addition, the invention features polynucleotide sequences which hybridize under stringent conditions to SEQ ID NO:4 and SEQ ID NO:6.

The invention additionally features fragments or portions of the nucleic acid sequences encoding the claimed polypeptides, and expression vectors and host cells comprising polynucleotides that encode BCRP. The present invention also features antibodies which bind specifically to BCRP, and pharmaceutical compositions comprising substantially purified BCRP. The invention also features the use of agonists and antagonists of BCRP. The invention also features a method for treating cancer using antagonists of BCRP1, BCRP2, and agonists of BCRP2; for treating immunological disorders using antagonists of BCRP1; and for treating disorders associated with cell growth and differentiation using BCRP 1.

BRIEF DESCRIPTION OF THE FIGURES

FIG. 1A, 1B, and 1C show the amino acid sequence (SEQ ID NO:1) and nucleic acid sequence (SEQ ID NO:2) of BCRP1. The alignment was produced using MacDNASIS PRO™ software (Hitachi Software Engineering Co., Ltd., San Bruno, Calif.).

FIGS. 2A, 2B, 2C and 2D show the amino acid sequence (SEQ ID NO:3) and nucleic acid sequence (SEQ ID NO:4) of BCRP2. The alignment was produced using MacDNASIS PRO™ software (Hitachi Software Engineering Co., Ltd., San Bruno, Calif.).

Figure 3:
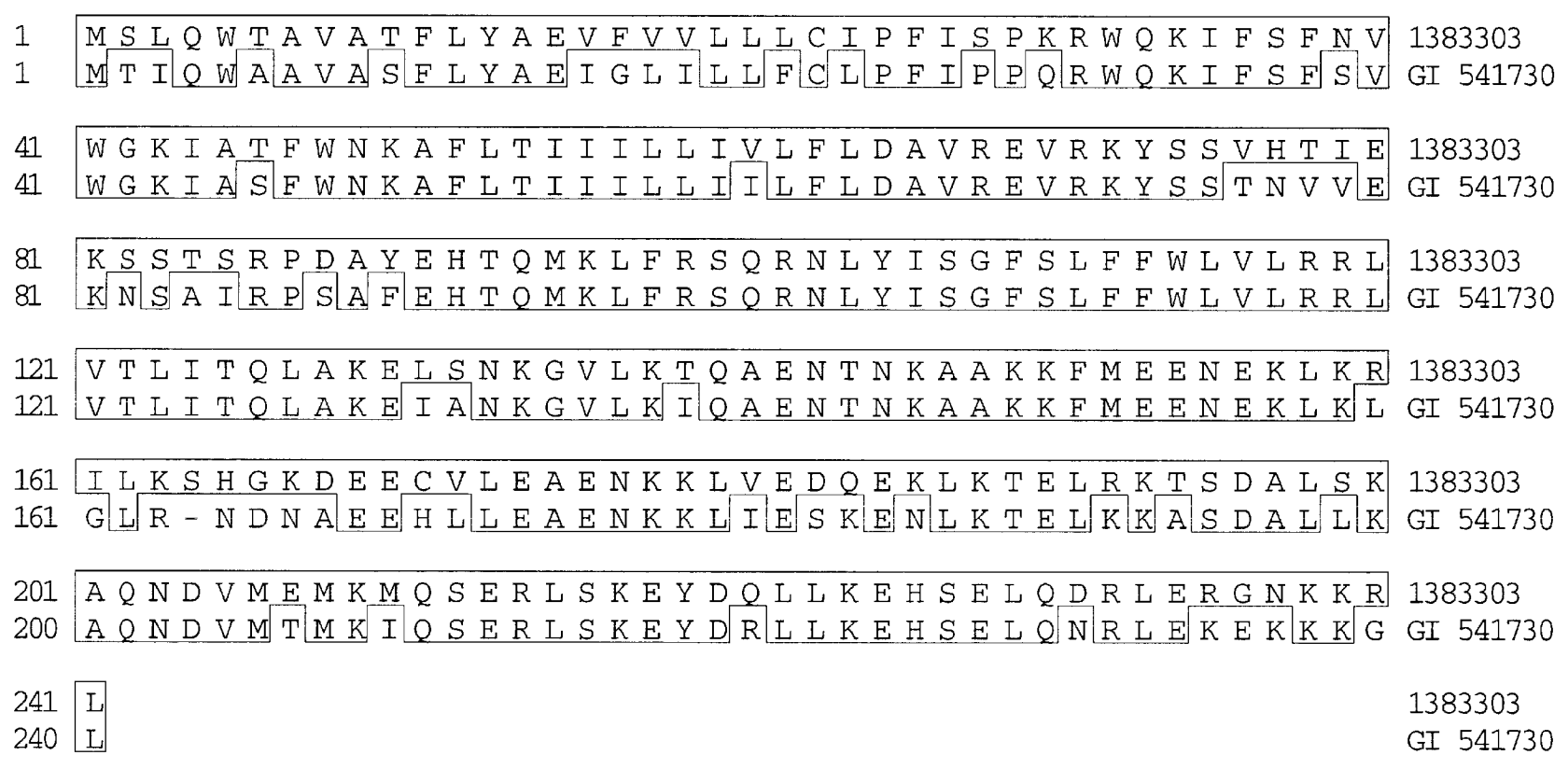

FIG. 3 shows the amino acid sequence alignments between BCRP1 (SEQ ID NO:1) an d mouse BAP 29 (GI 541730, SEQ ID NO:7). The alignment was produced using the multisequence alignment program of DNASTAR™ software (DNASTAR Inc, Madison Wis.).

FIGS. 4A and 4B show the amino acid sequence alignments between BCRP2 (SEQ ID NO:3), BCRP2 variant (SEQ ID NO:5) and mouse BAP 29 (GI 541734, SEQ ID NO:8). The alignment was produced using the multisequence alignment program of DNASTAR™ software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"Nucleic acid sequence" as used herein refers to an oligonucleotide, nucleotide, or polynucleotide, and fragments or portions thereof, and to DNA or RNA of genomic or synthetic origin which may be single- or double-stranded, and represent the sense or complement or antisense strand. Similarly, "amino acid sequence" as used herein refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

BCRP, as used herein, refers to the amino acid sequences of substantially purified BCRP obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™ (Perkin Elmer, Norwalk, Conn.) in the 5' and/or the 3' direction and resequenced, or which has been assembled from the overlapping sequences of more than one Incyte clone using the GELVIEW™ Fragment Assembly system (GCG, Madison, Wis.), or which has been both extended and assembled.

A "variant" of BCRP, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively. The term "biologically active", as used herein, refers to a protein having structural, regulatory, or biochemical functions of a naturally occurring molecule. Likewise, "immunologically active" refers to the capability of the natural, recombinant, or synthetic BCRP, or any oligopeptide thereof, to induce a specific immune response in appropriate animals or cells and to bind with specific antibodies.

The term "agonist", as used herein, refers to a molecule which, when bound to BCRP, causes a change in BCRP which modulates the activity of BCRP. Agonists may include proteins, nucleic acids, carbohydrates, or any other molecules which bind to BCRP.

The terms "antagonist" or "inhibitor", as used herein, refer to a molecule which, when bound to BCRP, blocks or modulates the biological or immunological activity of BCRP. Antagonists and inhibitors may include proteins, nucleic acids, carbohydrates, or any other molecules which bind to BCRP.

The term "modulate", as used herein, refers to a change or an alteration in the biological activity of BCRP. Modulation may be an increase or a decrease in protein activity, a change in binding characteristics, or any other change in the biological, functional or immunological properties of BCRP.

The term "mimetic", as used herein, refers to a molecule, the structure of which is developed from knowledge of the structure of BCRP or portions thereof and, as such, is able to effect some or all of the actions of BCRP-like molecules.

The term "derivative", as used herein, refers to the chemical modification of a nucleic acid encoding BCkP or the encoded BCRP. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "hybridization", as used herein, refers to any process by which a strand of nucleic acid binds with a-complementary strand through base pairing.

The term "hybridization complex", as used herein, refers to a complex formed between two nucleic acid sequences by virtue of the formation of hydrogen binds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense or complementary molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense or complement strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human BCRP and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding BCRP or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 by northern analysis is indicative of the presence of mRNA encoding BCRP in a sample and thereby correlates with expression of the transcript from the polynucleotide encoding the protein.

"Alterations" in the polynucleotide of SEQ ID NO:2, as used herein, comprise any alteration in the sequence of polynucleotides encoding BCRP including deletions, insertions, and point mutations that may be detected using hybridization assays. Included within this definition is the detection of alterations to the genomic DNA sequence which encodes BCRP (e.g., by alterations in the pattern of restriction fragment length polymorphisms capable of hybridizing to SEQ ID NO:2), the inability of a selected fragment of SEQ ID NO:2 to hybridize to a sample of genomic DNA (e.g., using allele-specific oligonucleotide probes), and improper or unexpected hybridization, such as hybridization to a locus other than the normal chromosomal locus for the polynucleotide sequence encoding BCRP (e.g., using fluorescent in situ hybridization [FISH] to metaphase chromosomes spreads).

As used herein, the term "antibody" refers to intact molecules as well as fragments thereof, such as Fa, F(ab')$_2$, and Fv, which are capable of binding the epitopic determinant. Antibodies that bind BCRP polypeptides can be prepared using intact polypeptides or fragments containing small peptides of interest as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

The Invention

The invention is based on the discovery of two B-cell receptor associated proteins, (BCRP1 and BCRP2) and a variant of BCRP2, collectively referred to as BCRP, the polynucleotides encoding BCRP, and the use of these compositions for the diagnosis, prevention, or treatment of disorders associated with the expression of BCRP.

Nucleic acids encoding the human BCRP1 of the present invention were first identified in Incyte Clone 1383303 from the brain tumor cDNA library (BRAITUT08) through a computer search for amino acid sequence alignments. A consensus sequence, SEQ ID NO:2, was derived from the following overlapping and/or extended nucleic acid sequences: Incyte Clones; 1383303, 1385136 (BRAITUT08), 1002194 (BRSTNOT03), 1392554 (THYRNOT03), 1480614 (CORPNOT02), 1631701 (COLNNOT19), 462896 (LATRNOT01), 531583 (BRAINOT03), and 967961 (BRSTNOT05).

Nucleic acids encoding the human BCRP2 of the present invention were first identified in Incyte Clone 484722 from the teratocarcinoma cDNA library (HNT2RAT01) through a computer search for amino acid sequence alignments. A consensus sequence, SEQ ID NO:4, was derived from the following overlapping and/or extended nucleic acid sequences: Incyte Clones; 484722 (HNT2RAT01), 1354868 (LUNGNOT09), 161583 (ADENINB01), 272498 (LIVRNOT02), 344519 (THYMNOT02), 041573 (TBLYNOT01), 458853 (KERANOT01), 687606 (UTRSNOT02), 786831 (PROSNOT05), 871306 (LUNGAST01), 932480 (CERVNOT01), and 980758 (TONGTUT01).

Nucleic acids encoding the human BCRP2 variant of the present invention were first identified in Incyte Clone 454790 from the keratinocyte cell cDNA library (KERANOT01) through a computer-generated search for amino acid sequence alignments. A consensus sequence, SEQ ID NO:6, was derived from extension and assembly of nucleic acid sequences of Incyte Clone 454790 (KERANOT01), 1354868 (LUNGNOT09), 161583 (ADENINB01), 272498 (LIVRNOT02), 344519 (THYMNOT02), 041573 (TBLYNOT01), 458853 (KERANOT01), 687606 (UTRSNOT02), 786831 (PROSNOT05), 871306 (LUNGAST01), 932480 (CERVNOT01), and 980758 (TONGTUT01).

The BRAITU08 cDNA library was constructed from brain tumor tissue (specimen #0215; Mayo Clinic, Rochester, Minn.). The frozen tissue was homogenized and lysed using a Brinkmann Homogenizer Polytron PT-3000 (Brinkmann Instruments, Westbury, N.J.) in guanidinium isothiocyanate solution. The lysate was centrifuged over a 5.7 M CsCl cushion using an Beckman SW28 rotor in a Beckman L8-70M Ultracentrifuge (Beckman Instruments) for 18 hours at 25,000 rpm at ambient temperature. The RNA-was extracted with acid phenol pH 4.7, precipitated using 0.3 M sodium acetate and 2.5 volumes of ethanol, resuspended in RNAse-free water, and DNase treated at 37° C. The RNA extraction and precipitation were repeated as before. The mRNA was isolated with the Qiagen Oligotex kit (QIAGEN, Inc.; Chatsworth, Calif.) and used to construct the cDNA library.

Figure 4A:
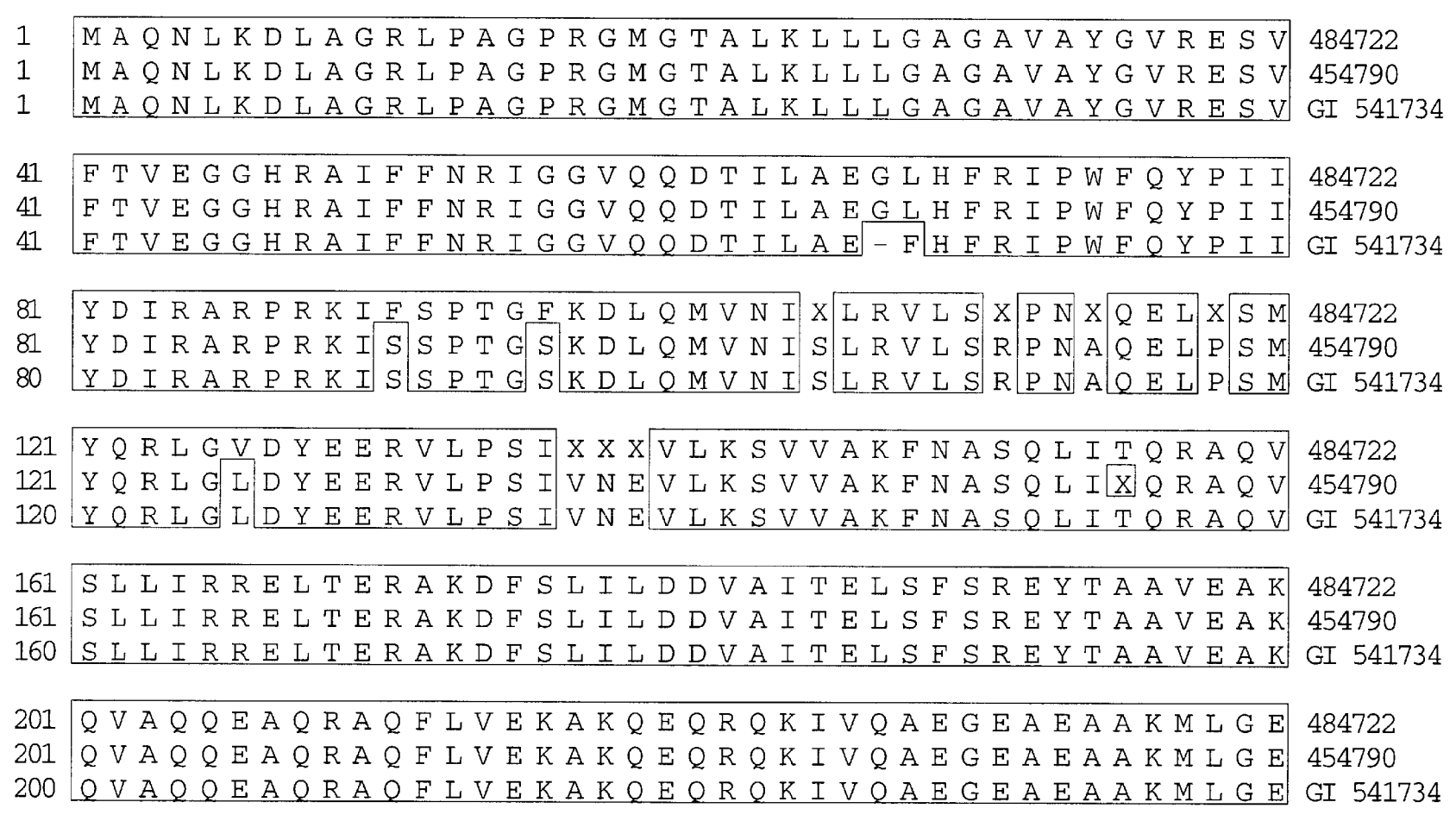
Figure 4B:
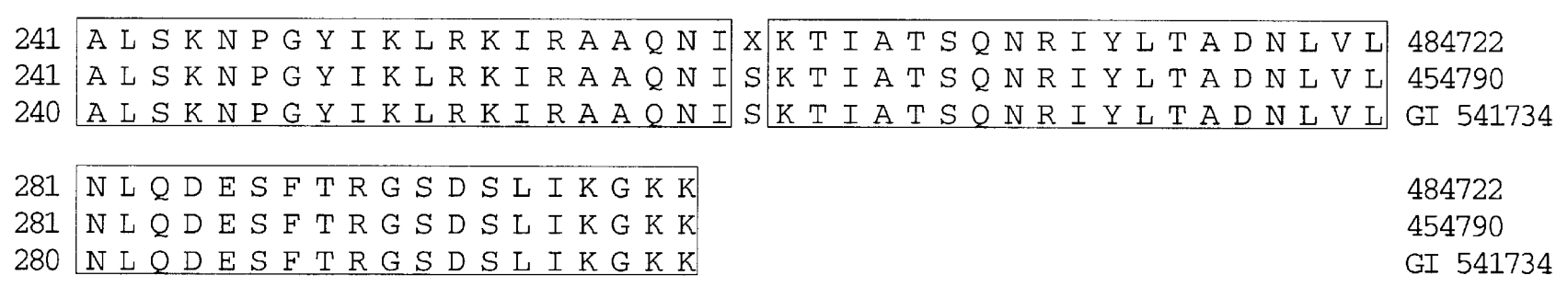

In another embodiment, the invention encompasses a polypeptide comprising the amino acid sequence of SEQ ID NO:3, as shown in FIGS. 2A, 2B, 2C, and 2D. BCRP2 is 299 amino acids in length and contains a potential N glycosylation site at $N_{149}$ and two potential protein kinase C phosphorylation sites at $T_{155}$ and $T_{169}$. As shown in FIGS. 4A and 4B, BCRP2 has chemical and structural homology with mouse BAP37 (SEQ ID NO:8), in particular, BCRP2 shares 97% identity with mouse BAP37.

The invention also encompasses BCRP variants, including the variant shown in SEQ ID NO:5. A preferred BCRP variant is one having at least 80%, and more preferably 90%, amino acid sequence identity to the BCRP1 amino acid sequence (SEQ ID NO:1) or the BCRP2 amino acid sequence (SEQ ID NO:3). A most preferred BCRP variant is one having at least 95% amino acid sequence identity to SEQ ID NO:1 or SEQ ID NO 3.

The invention also encompasses polynucleotides which encode BCRP. Accordingly, any nucleic acid sequence which encodes the amino acid sequence of BCRP can be used to generate recombinant molecules which express BCRP. In a particular embodiment, the invention encompasses the polynucleotide comprising the nucleic acid sequence of SEQ ID NO:2 as shown in FIG. 1A, 1B, and 1C, and SEQ ID NO:4 as shown in FIGS. 2A, 2B, 2C, and 2D.

It will be appreciated by those skilled in the art that as a result of the degeneracy of the genetic code, a multitude of nucleotide sequences encoding BCRP, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring BCRP, and all such variations are to be considered as being specifically disclosed.

Although nucleotide sequences which encode BCRP and its variants are preferably capable of hybridizing to the nucleotide sequence of the naturally occurring BCRP under appropriately selected conditions of stringency, it may be advantageous to produce nucleotide sequences encoding BCRP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding BCRP and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode BCRP and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding BCRP or any portion thereof.

Also encompassed by the invention are polynucleotide sequences that are capable of hybridizing to the claimed nucleotide sequences, and in particular, those shown in SEQ ID NO:2, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–511), and may be used at a defined stringency.

Altered nucleic acid sequences encoding BCRP which are encompassed by the invention include deletions, insertions, or substitutions of different nucleotides resulting in a polynucleotide that encodes the same or a functionally equivalent BCRP. The encoded protein may also contain deletions, insertions, or substitutions of amino acid residues which produce a silent change and result in a functionally equivalent BCRP. Deliberate amino acid substitutions may be made on the basis of similarity in polarity, charge, solubility, hydrophobicity, hydrophilicity, and/or the amphipathic nature of the residues as long as the biological activity of BCRP is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding BCRP. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, Sequenase® (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The nucleic acid sequences encoding BCRP may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (199 1) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PromoterFinder™ libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode BCRP, or fusion proteins or functional equivalents thereof, may be used in recombinant DNA molecules to direct expression of BCRP in appropriate host cells. Due to the inherent degeneracy of the genetic code, other DNA sequences which encode substantially the same or a functionally equivalent amino acid sequence may be produced and these sequences may be used to clone and express BCRP.

As will be understood by those of skill in the art, it may be advantageous to produce BCRP-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter BCRP encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding BCRP may be ligated to a heterologous sequence to encode a fusion protein. For example, to screen peptide libraries for inhibitors of BCRP activity, it may be useful to encode a chimeric BCRP protein that can be recognized by a commercially available antibody. A fusion protein may also be engineered to contain a cleavage site located between the BCRP encoding sequence and the heterologous protein sequence, so that BCRP may be cleaved and purified away from the heterologous moiety.

In another embodiment, sequences encoding BCRP may be synthesized, in whole or in part, using chemical methods well known in the art (see Caruthers, M. H. et al. (1980) Nucl. Acids Symp. Ser. 7:215–223, Horn, T. et al. (1980) Nucl. Acids Symp. Ser. 7:225–232). Alternatively, the protein itself may be produced using chemical methods to synthesize the amino acid sequence of BCRP, or a portion thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of BCRP, or any part thereof, may be altered during direct synthesis and/or combined using chemical methods with sequences from other proteins, or any part thereof, to produce a variant polypeptide.

In order to express a biologically active BCRP, the nucleotide sequences encoding BCRP or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding BCRP and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding BCRP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding BCRP, vectors based on SV40 or EBV may be used with an appropriate selectable marker.

In bacterial systems, a number of expression vectors may be selected depending upon the use intended for BCRP. For example, when large quantities of BCRP are needed for the induction of antibodies, vectors which direct high level expression of fusion proteins that are readily purified may be used. Such vectors include, but are not limited to, the multifunctional *E. coli* cloning and expression vectors such as Bluescript® (Stratagene), in which the sequence encoding BCRP may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding BCRP may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196).

An insect system may also be used to express BCRP. For example, in one such system, *Autographa califomica* nuclear polyhedrosis virus (ACNPV) is used as a vector to express foreign genes in *Spodoptera frugiperda* cells or in Trichoplusia larvae. The sequences encoding BCRP may be cloned into a non-essential region of the virus, such as the polyhedrin gene, and placed under control of the polyhedrin promoter. Successful insertion of BCRP will render the polyhedrin gene inactive and produce recombinant virus lacking coat protein. The recombinant viruses may then be used to infect, for example, *S. frugiperda* cells or Trichoplusia larvae in which BCRP may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding BCRP may be ligated into an adenovirus transcription/translation complex consisting of the late promoter and tripartite leader sequence. Insertion in a non-essential E1 or E3 region of the viral genome may be used to obtain a viable virus which is capable of expressing BCRP in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding BCRP. Such signals include the ATG initiation codon and adjacent sequences. In cases where sequences encoding BCRP, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probi. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational, activities, may be chosen to ensure the correct modification and processing of the foreign protein.

For long-term, high-yield production of recombinant proteins, stable expression is preferred. For example, cell lines which stably express BCRP may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding BCRP is inserted within a marker gene sequence, recombinant cells containing sequences encoding BCRP can be identified by the absence of marker gene function. Alternatively, a marker gene can be placed in tandem with a sequence encoding BCRP under the control of a single promoter. Expression of the marker gene in response to induction or selection usually indicates expression of the tandem gene as well.

Alternatively, host cells which contain the nucleic acid sequence encoding BCRP and express BCRP may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding BCRP can be detected by DNA-DNA or DNA-RNA hybridization or amplification using probes or portions or fragments of polynucleotides encoding BCRP. Nucleic acid amplification based assays involve the use of oligonucleotides or oligomers based on the sequences encoding BCRP to detect transformants containing DNA or RNA encoding BCRP. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of BCRP, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on BCRP is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding BCRP include oligolabeling, nick translation, end-labeling or PCR amplification using a labeled nucleotide. Alternatively, the sequences encoding BCRP, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding BCRP may be cultured under conditions suitable for the expression and recovery of the protein from cell culture.

The protein produced by a recombinant cell may be secreted or contained intracellularly depending on the sequence and/or the vector used. As will be understood by those of skill in the art, expression vectors containing polynucleotides which encode BCRP may be designed to contain signal sequences which direct secretion of BCRP through a prokaryotic or eukaryotic cell membrane. Other recombinant constructions may be used to join sequences encoding BCRP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and BCRP may be used to facilitate purification. One such expression vector provides for expression of a fusion protein containing BCRP and a nucleic acid encoding 6 histidine residues preceding a thioredoxin or an enterokinase cleavage site. The histidine residues facilitate purification on IMIAC (immobilized metal ion affinity chromatography as described in Porath, J. et al. (1992, Prot. Exp. Purif. 3: 263–281) while the enterokinase cleavage site provides a means for purifying BCRP from the fusion protein. A discussion of vectors which contain fusion proteins is provided in Kroll, D. J. et al. (1993; DNA Cell Biol. 12:441–453).

In to recombinant production, fragments of BCRP may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of BCRP may be chemically synthesized separately and combined using chemical methods to produce the full length molecule.

Therapeutics

Based on the chemical and structural homology between BCRP1 (SEQ ID NO:1) and mouse BAP 29 (SEQ ID NO:3) and between BCRP2 (SEQ ID NO:3) and mouse BAP 37, the BCRPs are B cell receptor associated proteins which have a role in signal transduction. BCR associated proteins control B cell responses by regulating cell differentiation, proliferation, signal transduction, and the internalization and processing of the B cell receptor-antigen complex. Proteins with similar signal transduction functions may be used to modulate cell growth, differentiation, maturation, and cellular responses to lymphokines and other extracellular signals. In Northern analysis, BCRP1 sequences are associated with cancerous and proliferating cells and tissues, and as such, may play a role in modulating cell growth and differentiation.

Therefore, in one embodiment, antagonists or inhibitors of BCRP1 may be administered to a subject to treat or prevent cancer. These cancers include, but are not limited to, adenocarcinoma, leukemia, lymphoma, melanoma, myeloma, sarcoma, and teratocarcinoma and particularly cancers of the adrenal gland, bladder, bone, brain, breast, cervix, gastrointestinal tract, heart, kidney, liver, lung, ovaries, pancreas, parathyroid, pituitary gland, prostate, salivary gland, spleen, stomach, thymus, thyroid, testes, and uterus.

In another embodiment, a vector expressing the complement or antisense of the polynucleotide encoding BCRP1 may be administered to a subject treat or prevent the cancers listed above. In one aspect, antibodies which are specific for BCRP may be used directly as an antagonist, or indirectly as a targeting or delivery mechanism for bringing a pharmaceutical agent to cells or tissue which express BCRP.

In another embodiment, antagonists or inhibitors of BCRP1 may be administered to a subject to treat or prevent an immunological disorder. These disorders include, but are not limited to, adult respiratory distress syndrome, allergies, asthma, atherosclerosis, arteriosclerosis, bronchitis, dermatomyositis, neurofibromatosis, prostate hyperplasia, polymyositis, and rheumatoid arthritis.

In another embodiment, a vector expressing the complement or antisense of the polynucleotide encoding BCRP1 may be administered to a subject treat or prevent the disorders of cell proliferation listed in the preceding paragraph.

In another embodiment, BCRP1 or a fragment or derivative thereof may be administered to a subject to treat or prevent disorders associated with cell growth and differentiation. These include, but are not limited to, Alzheimer's disease, heart attacks, osteoarthritis, osteoporosis, Parkinson's disease, rheumatoid arthritis, stroke, wound healing, and damage to heart and nerve cells caused by ischemia, free radicals, and toxins.

In another embodiment, a vector capable of expressing BCRP1, or a fragment or a derivative thereof, may also be administered to a subject to treat or prevent the disorders associated with cell growth and differentiation listed in the preceding paragraph.

In another embodiment, agonists of BCRP1 may be administered to a subject to treat or prevent the disorders associated with cell growth and differentiation listed above. BCRP2 expression may induce apoptosis and may be used to selectively eliminate cells and tissues. Therefore, in one embodiment, BCRP2 or a fragment or derivative thereof may be administered to a subject to treat a disorder of cell growth, including cancer. These cancers include, but are not limited to, adenocarcinoma, leukemia, lymphoma, melanoma, myeloma, sarcoma, and teratocarcinoma and particularly cancers of the adrenal gland, bladder, bone, brain, breast, cervix, gastrointestinal tract, heart, kidney, liver, lung, ovaries, pancreas, parathyroid, pituitary gland, prostate, salivary gland, spleen, stomach, thymus, thyroid, testes, and uterus.

In another embodiment, a vector capable of expressing BCRP2, or a fragment or a derivative thereof, may also be administered to a subject to treat a disorder of cell growth and particularly those listed in the preceding paragraph.

In other embodiments, any of the therapeutic proteins, antagonists, antibodies, agonists, antisense or complement sequences or vectors described above may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of BCRP may be produced using methods which are generally known in the art. In particular, purified BCRP may be used to produce antibodies or to screen libraries of pharmaceutical agents to identify those which specifically bind BCRP.

Antibodies to BCRP may be generated using methods that are well known in the art. Such antibodies may include, but are not limited to, polyclonal, monoclonal, chimeric, single chain, Fab fragments, and fragments produced by a Fab expression library. Neutralizing antibodies, (i.e.,. those which inhibit dimer formation) are especially preferred for therapeutic use.

For the production of antibodies, various hosts including goats, rabbits, rats, mice, humans, and others, may be immunized by injection with BCRP or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to BCRP have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of BCRP amino acids may be fused with those of another protein such as keyhole limpet hemocyanin and antibody produced against the chimeric molecule.

Monoclonal antibodies to BCRP may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 0:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452454). Alternatively, techniques described for the production of single chain antibodies may be adapted, using methods known in the art, to produce BCRP-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:10134–10137).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for BCRP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between BCRP and its specific antibody. A two-site, monoclonal-based immunoassay utilizing monoclonal antibodies reactive to two non-interfering BCRP epitopes is preferred, but a competitive binding assay may also be employed (Maddox, supra).

In another embodiment of the invention, the polynucleotides encoding BCRP, or any fragment thereof, or antisense or complement molecules, may be used for therapeutic purposes. In one aspect, antisense or complement to the polynucleotide encoding BCRP may be used in situations in which it would be desirable to block the transcription of the mRNA. In particular, cells may be transformed with sequences complementary to polynucleotides encoding BCRP. Thus, antisense or complement molecules may be used to modulate BCRP activity, or to achieve regulation of gene function. Such technology is now well known in the art, and sense or antisense or complement oligomers or larger fragments, can be designed from various locations along the coding or control regions of sequences encoding BCRP.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding BCRP. These techniques are described both in Sambrook et al. (supra) and in Ausubel et al. (supra).

Genes encoding BCRP can be turned off by transforming a cell or tissue with expression vectors which express high levels of a polynucleotide or fragment thereof which encodes BCRP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding BCRP, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding BCRP.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding BCRP. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2'O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of BCRP, antibodies to BCRP, mimetics, agonists, antagonists, or inhibitors of BCRP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 MM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of BCRP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example BCRP or fragments thereof, antibodies of BCRP, agonists, antagonists or inhibitors of BCRP, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind BCRP may be used for the diagnosis of conditions or diseases characterized by expression of BCRP, or in assays to monitor patients being treated with BCRP, agonists, antagonists or inhibitors. The antibodies useful for diagnostic purposes may be prepared in the same manner as those described above for therapeutics. Diagnostic assays for BCRP include methods which utilize the antibody and a label to detect BCRP in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring BCRP are known in the art and provide a basis for diagnosing altered or abnormal levels of BCRP expression. Normal or standard values for BCRP expression are established by combining body fluids or cell extracts taken from normal mammalian subjects, preferably human, with antibody to BCRP under conditions suitable for complex formation. The amount of standard complex formation may be quantified by various methods, but preferably by photometric means. Quantities of BCRP expressed in subject samples, control and disease, from biopsied tissues are compared with the standard values. Deviation between standard and subject values establishes the parameters for diagnosing disease.

In another embodiment of the invention, the polynucleotides encoding BCRP may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of BCRP may be correlated with disease. The diagnostic assay may be used to distinguish between absence, presence, and excess expression of BCRP, and to monitor regulation of BCRP levels during therapeutic intervention.

In one aspect, hybridization with PCR probes which are capable of detecting polynucleotide sequences, including genomic sequences, encoding BCRP or closely related molecules, may be used to identify nucleic acid sequences which encode BCRP. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding BCRP, alleles, or related sequences.

Probes may also be used for the detection of related sequences, and should preferably contain at least 50% of the nucleotides from any of the BCRP encoding sequences. The hybridization probes of the subject invention may be DNA or RNA and derived from the nucleotide sequence of SEQ ID NO:2 or from genomic sequence including promoter, enhancer elements, and introns of the naturally occurring BCRP.

Means for producing specific hybridization probes for DNAs encoding BCRP include the cloning of nucleic acid sequences encoding BCRP or BCRP derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding BCRP may be used for the diagnosis of disorders which are associated with expression of BCRP. Examples of such conditions or diseases include, but are not limited to, cancers such as adenocarcinoma, leukemia, lymphoma, melanoma, myeloma, sarcoma, and teratocarcinoma and particularly cancers of the adrenal gland, bladder, bone, brain, breast, cervix, esophagus, gastrointestinal tract, heart, kidney, liver, lung, ovaries, pancreas, parathyroid, pituitary gland, prostate, salivary gland, spleen, stomach, thymus, thyroid, testes, and uterus; disorders of cell growth and proliferation such as adult respiratory distress syndrome, allergies, asthma, atherosclerosis, arteriosclerosis, bronchitis, dermatomyositis, neurofibromatosis, polymyositis, rheumatoid arthritis, Alzheimer's disease, heart attacks, osteoarthritis, osteoporosis, Parkinson's disease, stroke, damage to cells such as heart muscle, and nerve cells caused by ischemia, free radicals, and toxins; rheumatoid arthritis, wound healing. The polynucleotide sequences encoding BCRP may be used in Southern or northern analysis, dot blot, or other membrane-based technologies; in PCR technologies; or in dip stick, pin, ELISA or chip assays utilizing fluids or tissues from patient biopsies to detect altered BCRP expression. Such qualitative or quantitative methods are well known in the art.

In a particular aspect, the nucleotide sequences encoding BCRP may be useful in assays that detect activation or induction of various cancers, particularly those mentioned above. The nucleotide sequences encoding BCRP may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding BCRP in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of BCRP, a normal or standard profile for expression is established. This may be accomplished by combining body fluids or cell extracts taken from normal subjects, either animal or human, with a sequence, or a fragment thereof, which encodes BCRP, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding BCRP may involve the use of PCR. Such oligomers may be chemically synthesized, generated enzymatically, or produced from a recombinant source. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of BCRP include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or calorimetric response gives rapid quantitation.

In another embodiment of the invention, the nucleic acid sequences which encode BCRP may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding BCRP on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, BCRP, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between BCRP and the agent being tested, may be measured.

Another technique for drug screening which may be used provides for high throughput screening of compounds having suitable binding affinity to the protein of interest as described in published PCT application WO84/03564. In this method, as applied to BCRP large numbers of different small test compounds are synthesized on a solid substrate, such as plastic pins or some other surface. The test compounds are reacted with BCRP, or fragments thereof, and washed. Bound BCRP is then detected by methods well known in the art. Purified BCRP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding BCRP specifically compete with a test compound for binding BCRP. In this manner, the antibodies can be used to detect the presence of any peptide which shares one or more antigenic determinants with BCRP.

In additional embodiments, the nucleotide sequences which encode BCRP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention. EXAMPLES I cDNA Library Construction
BRAITUT08
The BRAITUT08 cDNA library was constructed from brain tumor tissue. (specimen #0215; Mayo Clinic, Rochester, MN). The frozen tissue was homogenized and lysed using a Brinkmann Homogenizer Polytron PT-3000 (Brinkmann Instruments, Westbury, N.J.) in guanidinium isothiocyanate solution. The lysate was centrifuged over a 5.7 M CsCl cushion using an Beckman SW28 rotor in a Beckman L8–70M Ultracentrifuge (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and DNase treated at 37° C. The RNA extraction and precipitation were repeated as before. The mRNA was isolated with the Qiagen Oligotex kit (QIAGEN, Inc.; Chatsworth, Calif.) and used to construct the cDNA library.

The mRNA was handled according to the recommended protocols in the SuperScript Plasmid System for cDNA Synthesis and Plasmid Cloning (Cat. #18248-013, Gibco BRL).

BRAITUT08 cDNAs were fractionated on a Sepharose CL4B column (Cat. #275105-01, Pharmacia), and those cDNAs exceeding 400 bp were ligated into pINCY I. The plasmid pINCY I was subsequently transformed into DH5α™ competent cells (Cat. #18258-012, Gibco BRL).
HNT2RAT01
The HNT2RAT01 cDNA library was constructed at Stratagene (STR937231), using RNA isolated from the hNT2 cell line derived from a human teratocarcinoma that exhibited properties characteristic of a committed neuronal precursor at an early stage of development. Cells were treated with 10 μM retinoic acid for 24 hours to create cells whose differentiation process may have commenced as described in Andrews, P. W. (1984) Dev. Biol., 103:285— 293. First strand cDNA synthesis was accomplished using an oligo d(T) primer/linker which also contained an XhoI restriction site. Second strand synthesis was performed using a combination of DNA polymerase I, E. coli ligase and RNase H, followed by the addition of an EcoRI adaptor to the blunt ended cDNA. The EcoRI adapted, double-stranded cDNA was then digested with XhoI restriction enzyme and fractionated to obtain sequences which exceeded 800 bp in size. The cDNAs were inserted into the LambdaZap® vector system (Stratagene); and the vector which contains the pBluescript™ phagemid (Stratagene) was transformed into E. coli host cells strain XLI-BlueMRF™ (Stratagene).

The phagemid forms of individual cDNA clones were obtained by the in vivo excision process. Enzymes from both pBluescript and a cotransformed f1 helper phage nicked the DNA, initiated new DNA synthesis, and created the smaller, single-stranded circular phagemid molecules which contained the cDNA insert. The phagemid DNA was released, purified, and used to reinfect fresh host cells (SOLR, Stratagene). Presence of the phagemid which carries the gene for 3-lactamase allowed transformed bacteria to grow on medium containing ampicillin.
KERANOT01
The keratinocyte culture used for the KERANOT01 library construction was derived from the leg skin of 22-week male fetus (Lot # CC2503; 2859-1) obtained from Clonetics Corp, San Diego Calif.). The cells were washed twice in phosphate buffered saline and lysed immediately in a buffer containing guanidinium isothiocyanate. The lysate was. extracted twice with phenol chloroform and centrifuged over a CsCl cushion using an Beckman SW28 rotor and a Beckman L8-70M Ultracentrifuge (Beckman Instruments). The poly A+RNA was precipitated using 0.3 M sodium acetate and 2.5 volumes of ethanol, resuspended in water, DNase treated for 15 min at 37° C., and isolated using the Qiagen Oligotex kit (QIAGEN Inc, Chatsworth Calif.).

First strand cDNA synthesis and isolation of the phagemid forms of individual cDNA clones was accomplished using the procedure described above for the HNT2RAT01 cDNA library.

II Isolation and Sequencing of cDNA Clones
BRAITUT08

Plasmid DNA was released from the cells and purified using the REAL Prep 96 Plasmid Kit (Catalog #26173; QIAGEN, Inc.). The recommended protocol was employed except for the following changes: 1) the bacteria were cultured in 1 ml of sterile Terrific Broth (Catalog #22711, GIBCO/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

HNT2RAT01, KERANOT01

Plasmid DNA was released from the cells and purified using the Miniprep Kit (Catalogue #77468; Advanced Genetic Technologies Corporation, Gaithersburg MD). This kit consists of a 96 well block with reagents for 960 purifications. The recommended protocol was employed except for the following changes: 1) the 96 wells were each filled with only 1 ml of sterile Terrific Broth (Catalog #2271 1, GIBCO/BRL, Gaithersburg Md.) with carbenicillin at 25 mg/L and glycerol at 0.4%; 2) the bacteria were cultured for 24 hours after the wells were inoculated and then lysed with 60 μl of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

Alternative methods of purifying plasmid DNA include the use of MAGIC MINIPREPS™ DNA Purification System (Catalogue #A7100, Promega, Madison Wis.) or QIAwell™-8 Plasmid, QiAwell PLUS DNA and QIAwell ULTRA DNA Purification Systems (QIAGEN® Chatsworth Calif.).

All of the cDNAs were sequenced by the method of Sanger F and AR Coulson (1975; J Mol Biol 94:441f), using a Hamilton Micro Lab 2200 (Hamilton, Reno Nev.) in combination with four Peltier Thermal Cyclers (PTC200 from MJ Research, Watertown Mass.) and Applied Biosystems 377 or 373 DNA Sequencing Systems (Perkin Elmer) and reading frame was determined.

III Homology Searching of CDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul, S. F. (1993) J. Mol. Evol. 36:290–300; Altschul et al. (1990) J. Mol. Biol. 215:403–410).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith RF and TF Smith (1992; Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin, S. and S. F. Altschul (1993; Proc Nat. Acad. Sci. 90:5873–5877) and incorporated herein by reference, searches for matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and mammalian sequences (mam), and deduced amino acid sequences from the same clones are searched against Gen-Bank functional protein databases, mammalian (mamp), vertebrate (vrtp) and eukaryote (eukp), for homology. The relevant database for a particular match were reported as a Glxxx±p (where xxx is pri, rod, etc and if present, p=peptide). Product score, the calculation of which is shown below, was used to determine the electronic stringency. For an exact match, product score was set at 70 with a conservative lower limit set at approximately 40 (1–2% error due to uncalled bases).

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as Gen-Bank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding BCRP occurs. Abundance and percent abundance are also reported. Abundance directly reflects the number of times a particular transcript is represented in a cDNA library, and percent abundance is abundance divided by the total number of sequences examined in the cDNA library.

V Extension of BCRP-Encoding Polynucleotides

Nucleic acid sequence of Incyte clone 1383303 (SEQ ID NO:2), Incyte clone 484722 or (SEQ ID NO:4), or Incyte clone 454790 or (SEQ ID NO:6) is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used-to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M. J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for; 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQuick™ (QIAGEN Inc., Chatsworth, Calif.). After recovery of the DNA, Kienow enzyme is used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 µl of SOC medium (Sambrook et al., supra).

After incubation for one hour at 37° C., the whole transformation mixture is plated on Luria Bertani (LB)-agar (Sambrook et al., supra) containing 2×Carb. The following day, several colonies are randomly picked from each plate and cultured in 150 µl of liquid LB/2×Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer, and one or both of the gene specific primers used for the extension reaction are added to each well. Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 µCi of [$\gamma$-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1 ×saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Complementary Polynucleotides

Sequence complementary to the BCRP-encoding sequence, or any part thereof, is used to decrease or inhibit expression of naturally occurring BCRP. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of BCRP, SEQ ID NO:1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the ABBR-encoding transcript.

VIII Expression of BCRP

Expression of BCRP is accomplished by subcloning the cDNAs into appropriate vectors and transforming the vectors into host cells. In this case, the cloning vector is used to express BCRP in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of BCRP into the bacterial growth media which can be used directly in the following assay for activity.

IX Demonstration of BCRP Activity

BCRP activity may be demonstrated by transfection of a mammalian cell line such as BW5147, Sp6, MEL 1, or P815 (ATCC) with eukaryotic expression vectors encoding BCRP Eukaryotic expression vectors are commercially available, and the techniques to introduce them into cells are well known to those skilled in the art. The cells are incubated for 48–72 hours after transformation under conditions appropriate for the cell line to allow expression and accumulation of BCRP. The transformed cells are stimulated by cross-linking the surface receptors by adding either anti-IgM, anti-IgD (Santa Cruz Biotechnology, Inc., Santa Cruz, Calif.), or both to the cell culture media. Cells are incubated in the presence of antibody and assayed for apoptosis by the TUNEL assay (Boehringer Mannheim Corp., Indianapolis, Ind., USA), or for cell proliferation, using a BrdU cell proliferation ELISA (Boehringer Mannheim). The results are evaluated by comparison with mock-transfected and unstimulated cell controls.

X Production of BCRP Specific Antibodies

BCRP that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431 A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex incomplete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring BCRP Using Specific Antibodies

Naturally occurring or recombinant BCRP is substantially purified by immunoaffinity chromatography using antibodies specific for BCRP. An immunoaffinity column is constructed by covalently coupling BCRP antibody to an activated chromatographic resin, such as CnBr-activated Sepharose (Pharmacia & Upjohn). After the coupling, the resin is blocked and washed according to the manufacturer's instructions.

Media containing BCRP is passed over the immunoaffinity column, and the column is washed under conditions that allow the preferential absorbance of BCRP (e.g., high ionic strength buffers in the presence of detergent). The column is eluted under conditions that disrupt antibody/BCRP binding (eg, a buffer of pH 2–3 or a high concentration of a chaotrope, such as urea or thiocyanate ion), and BCRP is collected.

XII Identification of Molecules Which Interact with BCRP

BCRP or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled BCRP, washed and any wells with labeled BCRP complex are assayed. Data obtained using different concentrations of BCRP are used to calculate values for the number, affinity, and association of BCRP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated polynucleotide sequence encoding a polypeptide comprising the amino acid sequence of SEQ ID NO:3 or SEQ ID NO:5.

2. A hybridization probe comprising the polynucleotide sequence of claim 1.

3. An isolated polynucleotide sequence comprising SEQ ID NO:4.

4. A polynucleotide sequence which is completely complementary to the polynucleotide sequence of claim 1.

5. A hybridization probe comprising the polynucleotide sequence of claim 4.

6. An expression vector containing the polynucleotide sequence of claim 1.

7. A host cell containing the vector of claim 6.

8. An isolated polynucleotide comprising a sequence selected from the group consisting of:
  a) a polynucleotide sequence of SEQ ID NO:4,
  b) a polynucleotide sequence of SEQ ID NO:6,
  c) a polynucleotide sequence completely complementary to a), and
  d) a polynucleotide sequence completely complementary to b).

9. A method for producing a polypeptide, the method comprising:
  a) culturing the host cell of claim 7 under conditions suitable for the expression of the polypeptide; and
  b) recovering the polypeptide from the host cell culture.

10. A method for detecting the expression of a nucleic acid in a sample comprising:
  a) hybridizing the polynucleotide of claim 2 to nucleic acids of the sample, thereby forming hybridization complexes; and
  b) comparing hybridization complex formation with a standard, wherein the comparison indicates expression of the nucleic acid in the sample.

11. The method of claim 10 further comprising amplifying the nucleic acids of the sample prior to hybridization.

* * * * *

SEQUENCE LISTING

<160> NUMBER OF SEQ ID NOS: 10

<210> SEQ ID NO 1
<211> LENGTH: 240
<212> TYPE: PRT
<213> ORGANISM: Homo sapiens
<220> FEATURE:
<221> NAME/KEY: misc_feature
<223> OTHER INFORMATION: Incyte Clone No: 1383303

<400> SEQUENCE: 1

```
Met Ser Leu Gln Trp Thr Ala Val Ala Thr Phe Leu Tyr Ala Glu Val
  1               5                  10                  15

Phe Val Val Leu Leu Cys Ile Pro Phe Ile Ser Pro Lys Arg Trp
                 20                  25                  30

Gln Lys Ile Phe Ser Phe Asn Val Trp Gly Lys Ile Ala Thr Phe Trp
             35                  40                  45

Asn Lys Ala Phe Leu Thr Ile Ile Leu Leu Ile Val Leu Phe Leu
 50                  55                  60

Asp Ala Val Arg Glu Val Arg Lys Tyr Ser Ser Val His Thr Ile Glu
 65                  70                  75                  80

Lys Ser Thr Ser Arg Pro Asp Ala Tyr Glu His Thr Gln Met Lys
                 85                  90                  95

Leu Phe Arg Ser Gln Arg Asn Leu Tyr Ile Ser Gly Phe Ser Leu Phe
                100                 105                 110

Phe Trp Leu Val Leu Arg Arg Leu Val Thr Leu Ile Thr Gln Leu Ala
             115                 120                 125

Lys Glu Leu Ser Asn Lys Gly Val Leu Lys Thr Gln Ala Glu Asn Thr
130                 135                 140

Asn Lys Ala Ala Lys Lys Phe Met Glu Glu Asn Glu Lys Leu Lys Arg
145                 150                 155                 160

Ile Leu Lys Ser His Gly Lys Asp Glu Glu Cys Val Leu Glu Ala Glu
                165                 170                 175

Asn Lys Lys Leu Val Glu Asp Gln Glu Lys Leu Lys Thr Glu Leu Arg
                180                 185                 190

Lys Thr Ser Asp Ala Leu Ser Lys Ala Gln Asn Asp Val Met Glu Met
            195                 200                 205

Lys Met Gln Ser Glu Arg Leu Ser Lys Glu Tyr Asp Gln Leu Leu Lys
    210                 215                 220

Glu His Ser Leu Gln Asp Arg Leu Glu Arg Gly Asn Lys Lys Arg Leu
225                 230                 235                 240
```

<210> SEQ ID NO 2
<211> LENGTH: 946
<212> TYPE: DNA
<213> ORGANISM: Homo sapiens
<220> FEATURE:
<221> NAME/KEY: misc_feature
<223> OTHER INFORMATION: Incyte Clone No: 1383303

<400> SEQUENCE: 2

```
tgctgtggga gagttcggtt gctgcggcgg ggcctgcacg ttgactgtgg gaaactcgga     60
aacaagctca catcttcctg tgggaaacct tctagcaaca ggatgagtct gcagtggact    120
gcagttgcca ccttcctcta tgcggaggtc tttgttgtgt tgcttctctg cattcccttc    180
atttctccta aaagatggca gaagattttt tcatttaatg tctggggtaa aattgcaact    240
```

-continued

```
ttttggaaca aggctttcct taccattatc atcctattga ttgttctatt tctagatgct    300
gtgagagaag taaggaaata ttcctcagtt cataccattg agaagagctc caccagcaga    360
cctgatgcct atgaacacac acagatgaaa cttttaggt ctcaaagaaa tctttacatt     420
tctggatttt ccctattttt ttggctagtt ttgagacgtc tggttacgct tattactcaa    480
ctggcaaaag aactgtcaaa caaaggtgta cttaaaactc aagcagaaaa tactaacaag    540
gctgccaaaa aatttatgga agaaaacgaa aaactaaaaa ggattttgaa aagccatggt    600
aaagatgaag aatgtgtttt ggaagcagaa aataaaaaac tagtagaaga ccaggagaaa    660
ctgaaaactg aattaaggaa gacttcagat gcccttttcta aggcacaaaa tgatgtgatg    720
gaaatgaaga tgcagtcaga gagactttcg aaagaatatg atcaactcct gaaagaacac    780
tctgaacttc aggatcgttt agaaagaggc aacaagaaaa gactgtgaac tttataaaag    840
acacttgcaa tatactgtgt caaaatgata attttgttat gttagcctct agaaaattta    900
agttcagaaa aatgcactat gaccggttcg taatttttttt aatgcc                 946
```

<210> SEQ ID NO 3
<211> LENGTH: 299
<212> TYPE: PRT
<213> ORGANISM: Homo sapiens
<220> FEATURE:
<221> NAME/KEY: unsure
<222> LOCATION: 105, 111, 114, 118, 137, 138, 139, 261
<223> OTHER INFORMATION: unknown or other
<220> FEATURE:
<221> NAME/KEY: misc_feature
<223> OTHER INFORMATION: Incyte Clone No: 484722

<400> SEQUENCE: 3

```
Met Ala Gln Asn Leu Lys Asp Leu Ala Gly Arg Leu Pro Ala Gly Pro
1               5                   10                  15

Arg Gly Met Gly Thr Ala Leu Lys Leu Leu Leu Gly Ala Gly Ala Val
            20                  25                  30

Ala Tyr Gly Val Arg Glu Ser Val Phe Thr Val Glu Gly Gly His Arg
        35                  40                  45

Ala Ile Phe Phe Asn Arg Ile Gly Gly Val Gln Gln Asp Thr Ile Leu
    50                  55                  60

Ala Glu Gly Leu His Phe Arg Ile Pro Trp Phe Gln Tyr Pro Ile Ile
65                  70                  75                  80

Tyr Asp Ile Arg Ala Arg Pro Arg Lys Ile Phe Ser Pro Thr Gly Phe
                85                  90                  95

Lys Asp Leu Gln Met Val Asn Ile Xaa Leu Arg Val Leu Ser Xaa Pro
            100                 105                 110

Asn Xaa Gln Glu Leu Xaa Ser Met Tyr Gln Arg Leu Gly Val Asp Tyr
        115                 120                 125

Glu Glu Arg Val Leu Pro Ser Ile Xaa Xaa Xaa Val Leu Lys Ser Val
    130                 135                 140

Val Ala Lys Phe Asn Ala Ser Gln Leu Ile Thr Gln Arg Ala Gln Val
145                 150                 155                 160

Ser Leu Leu Ile Arg Arg Glu Leu Thr Glu Arg Ala Lys Asp Phe Ser
                165                 170                 175

Leu Ile Leu Asp Asp Val Ala Ile Thr Glu Leu Ser Phe Ser Arg Glu
            180                 185                 190

Tyr Thr Ala Ala Val Glu Ala Lys Gln Val Ala Gln Gln Glu Ala Gln
        195                 200                 205

Arg Ala Gln Phe Leu Val Glu Lys Ala Lys Gln Glu Gln Arg Gln Lys
```

```
              210                 215                 220
Ile Val Gln Ala Glu Gly Glu Ala Glu Ala Ala Lys Met Leu Gly Glu
225                 230                 235                 240

Ala Leu Ser Lys Asn Pro Gly Tyr Ile Lys Leu Arg Lys Ile Arg Ala
                245                 250                 255

Ala Gln Asn Ile Xaa Lys Thr Ile Ala Thr Ser Gln Asn Arg Ile Tyr
            260                 265                 270

Leu Thr Ala Asp Asn Leu Val Leu Asn Leu Gln Asp Glu Ser Phe Thr
        275                 280                 285

Arg Gly Ser Asp Ser Leu Ile Lys Gly Lys Lys
    290                 295

<210> SEQ ID NO 4
<211> LENGTH: 1223
<212> TYPE: DNA
<213> ORGANISM: Homo sapiens
<220> FEATURE:
<221> NAME/KEY: unsure
<222> LOCATION: 473, 490, 500, 511, 1134, 1216
<223> OTHER INFORMATION: a or g or c or t, unknown, or other
<220> FEATURE:
<221> NAME/KEY: misc_feature
<223> OTHER INFORMATION: Incyte Clone No: 484722

<400> SEQUENCE: 4
gggagggttt caaagggagc gcacttccgc tgcccttttct ttcgccagcc ttacgggccc      60
gaaccctcgt gtgaagggtg cagtacctaa gccggagcgg ggtagaggcg ggccggcacc     120
cccttctgac ctccagtgcc gccggcctca agatcagaca tggcccagaa cttgaaggac     180
ttggcgggac ggctgcccgc cgggcccggg gcatgggca cggccctgaa gctgttgctg      240
ggggccggcg ccgtggccta cggtgtgcgc gaatctgtgt tcaccgtgga aggcgggcac     300
agagccatct tcttcaatcg gatcggtgga gtgcagcagg acactatcct ggccgagggc     360
cttcacttca ggatcccttg gttccagtac cccattatct atgacattcg ggccagacct     420
cgaaaaatct tctcccctac agggttcaaa gacctacaga tggtgaatat ctncctgcga     480
gtgttgtctn gacccaatgn tcaggagctt nctagcatgt accagcggct aggggtggac     540
tacgaggaac gagtgttgcc gtccattkty aamgrggtgc tcaagagtgt ggtggccaag     600
ttcaatgcct cacagctgat cacccagcgg gcccaggtat ccctgttgat ccgccgggag     660
ctgacagaga gggccaagga cttcagcctc atcctggatg atgtggccat cacagagctg     720
agctttagcc gagagtacac agctgctgta gaagccaaac aagtggccca gcaggaggcc     780
cagcgggccc aattcttggt agaaaaagca agcaggaac agcggcagaa aattgtgcag      840
gccgagggtg aggccgaggc tgccaagatg cttggagaag cactgagcaa gaaccctggc     900
tacatcaaac ttcgcaagat tcgagcagcc cagaatatct ycaagacgat cgccacatca     960
cagaatcgta tctatctcac agctgacaac cttgtgctga acctacagga tgaaagtttc    1020 accagggaa gtgacagcct catcaagggt aagaaatgag cctagtcacc aagaactcca     1080
cccccagagg aagtggatct rcttctycag tttttgagga gccagccagg ggtncagcac    1140
agmcctaccc cggccyagta tcatgcgatg gtccccca acggtttcct gaaccctttt     1200
ggattaagga agactnaaga tag                                              1223

<210> SEQ ID NO 5
<211> LENGTH: 299
<212> TYPE: PRT
<213> ORGANISM: Homo sapiens
```

```
<220> FEATURE:
<221> NAME/KEY: unsure
<222> LOCATION: 155
<223> OTHER INFORMATION: unknown or other
<220> FEATURE:
<221> NAME/KEY: misc_feature
<223> OTHER INFORMATION: Incyte Clone No: 454790

<400> SEQUENCE: 5

Met Ala Gln Asn Leu Lys Asp Leu Ala Gly Arg Leu Pro Ala Gly Pro
 1               5                  10                  15

Arg Gly Met Gly Thr Ala Leu Lys Leu Leu Gly Ala Gly Ala Val
            20                  25                  30

Ala Tyr Gly Val Arg Glu Ser Val Phe Thr Val Glu Gly Gly His Arg
            35                  40                  45

Ala Ile Phe Phe Asn Arg Ile Gly Gly Val Gln Gln Asp Thr Ile Leu
50                  55                  60

Ala Glu Gly Leu His Phe Arg Ile Pro Trp Phe Gln Tyr Pro Ile Ile
65                  70                  75                  80

Tyr Asp Ile Arg Ala Arg Pro Arg Lys Ile Ser Ser Pro Thr Gly Ser
                85                  90                  95

Lys Asp Leu Gln Met Val Asn Ile Ser Leu Arg Val Leu Ser Arg Pro
            100                 105                 110

Asn Ala Gln Glu Leu Pro Ser Met Tyr Gln Arg Leu Gly Leu Asp Tyr
            115                 120                 125

Glu Glu Arg Val Leu Pro Ser Ile Val Asn Glu Val Leu Lys Ser Val
130                 135                 140

Val Ala Lys Phe Asn Ala Ser Gln Leu Ile Xaa Gln Arg Ala Gln Val
145                 150                 155                 160

Ser Leu Leu Ile Arg Arg Glu Leu Thr Glu Arg Ala Lys Asp Phe Ser
                165                 170                 175

Leu Ile Leu Asp Asp Val Ala Ile Thr Glu Leu Ser Phe Ser Arg Glu
            180                 185                 190

Tyr Thr Ala Ala Val Glu Ala Lys Gln Val Ala Gln Gln Glu Ala Gln
            195                 200                 205

Arg Ala Gln Phe Leu Val Glu Lys Ala Lys Gln Glu Gln Arg Gln Lys
210                 215                 220

Ile Val Gln Ala Glu Gly Glu Ala Glu Ala Ala Lys Met Leu Gly Glu
225                 230                 235                 240

Ala Leu Ser Lys Asn Pro Gly Tyr Ile Lys Leu Arg Lys Ile Arg Ala
                245                 250                 255

Ala Gln Asn Ile Ser Lys Thr Ile Ala Thr Ser Gln Asn Arg Ile Tyr
            260                 265                 270

Leu Thr Ala Asp Asn Leu Val Leu Asn Leu Gln Asp Glu Ser Phe Thr
            275                 280                 285

Arg Gly Ser Asp Ser Leu Ile Lys Gly Lys Lys
290                 295

<210> SEQ ID NO 6
<211> LENGTH: 1212
<212> TYPE: DNA
<213> ORGANISM: Homo sapiens
<220> FEATURE:
<221> NAME/KEY: unsure
<222> LOCATION: 1211
<223> OTHER INFORMATION: a or g or c or t, unknown, or other
<220> FEATURE:
<221> NAME/KEY: misc_feature
<223> OTHER INFORMATION: Incyte Clone No: 454790
```

<400> SEQUENCE: 6

```
gcacttccgc tgccctttct ttcgccagcc ttacgggccc gaaccctcgt gtgaagggtg     60
cagtacctaa gccggagcgg ggtagaggcg ggccggcacc cccttctgac ctccagtgcc    120
gccggcctca agatcagaca tggcccagaa cttgaaggac ttggcgggac ggctgcccgc    180
cgggccccgg ggcatgggca cggccctgaa gctgttgctg ggggccggcg ccgtggccta    240
cggtgtgcgc gaatctgtgt tcaccgtgga aggcgggcac agagccatct tcttcaatcg    300
gatcggtgga gtgcagcagg acactatcct ggccgagggc cttcacttca ggatcccttg    360
gttccagtac cccattatct atgacattcg ggccagacct cgaaaaatct cctcccctac    420
aggctccaaa gacctacaga tggtgaatat ctccctgcga gtkttgtctc gacccaatgc    480
tcaggagctt cctagcatgt accagcgcct agggctggac tacgaggaac gagtgttgcc    540
gtccattgtc aacgaggtgc tcaagagtgt ggtggccaag ttcaatgcct acagctgat    600
camccagcgg gcccaggtat ccctgttgat ccgccgggag ctgacagaga gggccaagga    660
cttcagcctc atcctggatg atgtggccat cacagagctg agytttagcc gagagtacac    720
agctgctgta gaagccaaac aagtggccca gcaggaggcc cagcgggccc aattcttggt    780
agaaaaagca agcaggaac agcggcagaa aattgtgcag gccagggtg aggccgaggc    840
tgccaagatg cttggagaag cactgagcaa gaaccctggc tacatcaaac ttcgcaagat    900
tcgagcagcc cagaatatct ccaagacgat cgccacatca cagaatcgta tctatctcac    960
agctgacaac cttgtgctga acctacagga tgaaagtttc accaggggaa gtgacagcct   1020
catcaagggt aagaaatgag cctagtcacc aagaactcca cccccagagg aagtggatct   1080
gcttcttcca gttttttgagg agccagccag gggtccagca cagccctacc ccgccccagt   1140
atcatgcgat ggtcccccaa aacggtttcc tgaaccctc ttggattaag gaagactgaa   1200
gactagcccc nc                                                      1212
```

<210> SEQ ID NO 7
<211> LENGTH: 239
<212> TYPE: PRT
<213> ORGANISM: Mus musculus
<220> FEATURE:
<221> NAME/KEY: misc_feature
<223> OTHER INFORMATION: GenBank ID No: g541730

<400> SEQUENCE: 7

```
Met Thr Ile Gln Trp Ala Ala Val Ala Ser Phe Leu Tyr Ala Glu Ile
 1               5                  10                  15

Gly Leu Ile Leu Leu Phe Cys Leu Pro Phe Ile Pro Gln Arg Trp
             20                  25                  30

Gln Lys Ile Phe Ser Phe Ser Val Trp Gly Lys Ile Ala Ser Phe Trp
         35                  40                  45

Asn Lys Ala Phe Leu Thr Ile Ile Leu Leu Ile Ile Leu Phe Leu
     50                  55                  60

Asp Ala Val Arg Glu Val Arg Lys Tyr Ser Ser Thr Asn Val Val Glu
 65                  70                  75                  80

Lys Asn Ser Ala Ile Arg Pro Ser Ala Phe Glu His Thr Gln Met Lys
                 85                  90                  95

Leu Phe Arg Ser Gln Arg Asn Leu Tyr Ile Ser Gly Phe Ser Leu Phe
            100                 105                 110

Phe Trp Leu Val Leu Arg Arg Leu Val Thr Leu Ile Thr Gln Leu Ala
        115                 120                 125
```

```
Lys Glu Ile Ala Asn Lys Gly Val Leu Lys Ile Gln Ala Glu Asn Thr
            130                 135                 140

Asn Lys Ala Ala Lys Phe Met Glu Asn Glu Lys Leu Lys Leu Gly
145                 150                 155                 160

Leu Arg Asn Asp Asn Ala Glu Glu His Leu Leu Glu Ala Glu Asn Lys
                165                 170                 175

Lys Leu Ile Glu Ser Lys Glu Asn Leu Lys Thr Glu Leu Lys Lys Ala
            180                 185                 190

Ser Asp Ala Leu Leu Lys Ala Gln Asn Asp Val Met Thr Met Lys Ile
            195                 200                 205

Gln Ser Glu Arg Leu Ser Lys Glu Tyr Asp Arg Leu Leu Lys Glu His
    210                 215                 220

Ser Glu Leu Gln Asn Arg Leu Glu Lys Glu Lys Lys Gly Leu
225                 230                 235
```

<210> SEQ ID NO 8
<211> LENGTH: 298
<212> TYPE: PRT
<213> ORGANISM: Mus musculus
<220> FEATURE:
<221> NAME/KEY: misc_feature
<223> OTHER INFORMATION: GenBank ID No: g541734

<400> SEQUENCE: 8

```
Met Ala Gln Asn Leu Lys Asp Leu Ala Gly Arg Leu Pro Ala Gly Pro
1               5                   10                  15

Arg Gly Met Gly Thr Ala Leu Lys Leu Leu Gly Ala Gly Ala Val
            20                  25                  30

Ala Tyr Gly Val Arg Glu Ser Val Phe Thr Val Glu Gly His Arg
            35                  40                  45

Ala Ile Phe Phe Asn Arg Ile Gly Gly Val Gln Gln Asp Thr Ile Leu
        50                  55                  60

Ala Glu Phe His Phe Arg Ile Pro Trp Phe Gln Tyr Pro Ile Ile Tyr
65                  70                  75                  80

Asp Ile Arg Ala Arg Pro Arg Lys Ile Ser Ser Pro Thr Gly Ser Lys
                85                  90                  95

Asp Leu Gln Met Val Asn Ile Ser Leu Arg Val Leu Ser Arg Pro Asn
            100                 105                 110

Ala Gln Glu Leu Pro Ser Met Tyr Gln Arg Leu Gly Leu Asp Tyr Glu
        115                 120                 125

Glu Arg Val Leu Pro Ser Ile Val Asn Glu Val Leu Lys Ser Val Val
    130                 135                 140

Ala Lys Phe Asn Ala Ser Gln Leu Ile Thr Gln Arg Ala Gln Val Ser
145                 150                 155                 160

Leu Leu Ile Arg Arg Glu Leu Thr Glu Arg Ala Lys Asp Phe Ser Leu
                165                 170                 175

Ile Leu Asp Asp Val Ala Ile Thr Glu Leu Ser Phe Ser Arg Glu Tyr
            180                 185                 190

Thr Ala Ala Val Glu Ala Lys Gln Val Ala Gln Gln Glu Ala Gln Arg
        195                 200                 205

Ala Gln Phe Leu Val Glu Lys Ala Lys Gln Glu Gln Arg Gln Lys Ile
    210                 215                 220

Val Gln Ala Glu Gly Glu Ala Glu Ala Ala Lys Met Leu Gly Glu Ala
225                 230                 235                 240

Leu Ser Lys Asn Pro Gly Tyr Ile Lys Leu Arg Lys Ile Arg Ala Ala
```

```
                        245                 250                 255
Gln Asn Ile Ser Lys Thr Ile Ala Thr Ser Gln Asn Arg Ile Tyr Leu
            260                 265                 270
Thr Ala Asp Asn Leu Val Leu Asn Leu Gln Asp Glu Ser Phe Thr Arg
        275                 280                 285
Gly Ser Asp Ser Leu Ile Lys Gly Lys Lys
    290                 295

<210> SEQ ID NO 9
<211> LENGTH: 4
<212> TYPE: PRT
<213> ORGANISM: Homo sapiens
<220> FEATURE:
<221> NAME/KEY: misc_feature
<223> OTHER INFORMATION: 000

<400> SEQUENCE: 9

Ile Thr Ala Met
1

<210> SEQ ID NO 10
<211> LENGTH: 4
<212> TYPE: PRT
<213> ORGANISM: Homo sapiens
<220> FEATURE:
<221> NAME/KEY: unsure
<222> LOCATION: 3
<223> OTHER INFORMATION: unknown or other
<220> FEATURE:
<221> NAME/KEY: misc_feature
<223> OTHER INFORMATION: 000

<400> SEQUENCE: 10

Asn Pro Xaa Tyr
1
```